US00PP21636P2

(12) United States Plant Patent
Meinl

(10) Patent No.: US PP21,636 P2
(45) Date of Patent: Jan. 18, 2011

(54) ***HYDRANGEA* PLANT NAMED 'HORABSTRA'**
(50) Latin Name: *Hydrangea macrophylla*
Varietal Denomination: HorAbstra

(75) Inventor: Katrin Meinl, Dresden (DE)

(73) Assignee: Claus +Tosten Kühne GbR, Dresden (DE)

( * ) Notice: Subject to any disclaimer, the term of this patent is extended or adjusted under 35 U.S.C. 154(b) by 0 days.

(21) Appl. No.: 12/653,195

(22) Filed: Dec. 9, 2009

(51) Int. Cl.
*A01H 5/00* (2006.01)

(52) U.S. Cl. ..... Plt./250
(58) Field of Classification Search ..... Plt./250
See application file for complete search history.

*Primary Examiner*—Annette H Para
(74) *Attorney, Agent, or Firm*—C. A. Whealy

(57) ABSTRACT

A new and distinct cultivar of *Hydrangea* plant named 'HorAbstra', characterized by its upright and mounded plant habit; black-colored stems; strong and dark green-colored leaves; and large lacecap-type inflorescences with dark pink-colored flowers.

2 Drawing Sheets

Botanical designation: *Hydrangea macrophylla.*
Cultivar denomination: 'HORABSTRA'.

BACKGROUND OF THE INVENTION

The present invention relates to a new and distinct cultivar of *Hydrangea* plant, botanically known as *Hydrangea macrophylla* and hereinafter referred to by the name 'HorAbstra'.

The new *Hydrangea* plant is a product of a planned breeding program conducted by the Inventor in Dresden, Germany. The objective of the breeding program was to develop new container-type *Hydrangea* plants with attractive foliage, stem and flower coloration.

The new *Hydrangea* plant originated from a cross-pollination in August, 2002 of a proprietary selection of *Hydrangea macrophylla* identified as code number 115-9711, not patented, as the female, or seed parent and an unnamed proprietary selection of *Hydrangea macrophylla,* not patented, as the male, or pollen, parent. The new *Hydrangea* plant was discovered and selected by the Inventor during the summer of 2004 as a flowering plant within the progeny of the stated cross-pollination in a controlled environment in Dresden, Germany.

Asexual reproduction of the new cultivar by softwood cuttings in Dresden, Germany since 2005 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'HorAbstra'. These characteristics in combination distinguish 'HorAbstra' as a new and distinct cultivar of *Hydrangea:*

1. Upright and mounded plant habit.
2. Black-colored stems.

3. Strong and dark green-colored leaves.
4. Large lacecap-type inflorescences with dark pink-colored flowers.

Plants of the new *Hydrangea* differ primarily from plants of the female parent selection in the following characteristics:

1. Plants of the new *Hydrangea* are more vigorous than plants of the female parent selection.
2. Plants of the new *Hydrangea* have black-colored stems whereas plants of the female parent selection have green-colored stems.
3. Plants of the new *Hydrangea* have dark pink-colored flowers whereas plants of the female parent selection have light pink-colored flowers.

Plants of the new *Hydrangea* differ primarily from plants of the male parent selection in the following characteristics:

1. Plants of the new *Hydrangea* are more vigorous than plants of the male parent selection.
2. Plants of the new *Hydrangea* have lacecap-type inflorescences whereas plants of the male parent selection have mophead-type inflorescences.

Plants of the new *Hydrangea* can be compared to plants of *Hydrangea* 'Nigra', not patented. Plants of the new *Hydrangea* differ primarily from plants of 'Nigra' in the following characteristics:

1. Plants of the new *Hydrangea* have longer internodes than plants of 'Nigra'.
2. Plants of the new *Hydrangea* have lacecap-type inflorescences whereas plants of 'Nigra' have mophead-type inflorescences.
3. Flowers of plants of the new *Hydrangea* have larger sepals than flowers of plants of 'Nigra'.

BRIEF DESCRIPTION OF THE PHOTOGRAPHS

The accompanying colored photographs illustrate the unique appearance of the new *Hydrangea* plant, showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'HorAbstra' grown in a container.

The photograph on the second sheet is a close-up view of a typical lateral branch and inflorescence of 'HorAbstra'.

DETAILED BOTANICAL DESCRIPTION

Plants used in the aforementioned photographs and in the following description were grown during the summer and autumn in Grand Haven, Mich. in an outdoor nursery and under conditions which closely approximate commercial production conditions. Plants of the new *Hydrangea* were three years old when the photographs and description were taken. In the following description, color references are made to The Royal Horticultural Society Colour Chart, 1995 Edition, except where general terms of ordinary dictionary significance are used.

Botanical description: *Hydrangea macrophylla* 'HorAbstra'.

Parentage:

*Female, or seed, parent.*—Proprietary selection of *Hydrangea macrophylla* identified as code number 115-9711, not patented.

*Male, or pollen, parent.*—Unnamed proprietary selection of *Hydrangea macrophylla,* not patented.

Propagation:

*Type cutting.*—By softwood cuttings.

*Time to initiate roots.*—About 18 days at temperatures of about 24° C.

*Time to produce a rooted young plant.*—About two months at temperatures of about 24° C.

*Root description.*—Fine to thick; creamy white in color.

*Rooting habit.*—Freely branching; dense.

Plant description:

*Form/growth habit.*—Perennial shrub; upright and mounded plant habit; broadly inverted triangle; freely branching habit; strong lateral branches; vigorous growth habit.

*Plant height.*—About 60 cm.

*Plant diameter or area of spread.*—About 25 cm.

*Lateral branches.*—Length: About 45 cm. Diameter: About 6 mm. Internode length: About 9 cm. Texture: Smooth, glabrous. Strength: Strong. Color: Close to 202A.

Foliage description:

*Arrangement.*—Opposite, simple.

*Length.*—About 14.5 cm.

*Width.*—About 8 cm.

*Shape.*—Broadly ovate.

*Apex.*—Broadly acute.

*Base.*—Obtuse to cuneate.

*Margin.*—Serrate.

*Texture, upper and lower surfaces.*—Smooth, glabrous; rugose.

*Venation pattern.*—Pinnate.

*Color.*—Developing and fully expanded leaves, upper surface: Close to 136A; venation, close to 137C. Developing and fully expanded leaves, lower surface: Close to 137C; midrib, close to 187A; lateral venation, close to 137C.

*Petiole.*—Length: About 3.5 cm. Diameter: About 4 mm. Texture, upper and lower surfaces: Smooth, glabrous. Color, upper and lower surfaces: Close to 187A.

Flower description:

*Flower type and habit.*—Single sterile and fertile flowers arranged on terminal lacecap-type panicles; fertile flowers face mostly upright and sterile flowers face upright to outwardly.

*Fragrance.*—None detected.

*Natural flowering season.*—Continuous flowering from June to September in Grand Haven, Mich.; early flowering habit, plants begin flowering about eleven weeks after planting.

*Flower longevity, fertile flowers.*—Flowers last about three weeks on the plant; flowers not persistent.

*Flower longevity, sterile flowers.*—Flowers last about one month on the plant; flowers persistent.

*Quantity of flowers.*—Freely flowering; about 237 fertile flowers and about 26 sterile flowers per panicle.

*Panicle height.*—About 10 cm.

*Panicle diameter.*—About 16 cm.

*Flower diameter, fertile flowers.*—About 1.4 cm.

*Flower depth (height), fertile flowers.*—About 8 mm.

*Flower diameter, sterile flowers.*—About 6 cm.

*Flower depth (height), sterile flowers.*—About 5 cm.

*Flower buds, fertile and sterile flowers.*—Length: About 4 mm. Diameter: About 3 mm. Shape: Obovate. Color: Close to 66D.

*Petals, fertile flowers only.*—Quantity/arrangement: Five in a single whorl. Length: About 5 mm. Width: About 3 mm to 4 mm. Shape: Ovate. Apex: Acute. Base: Attenuate. Margin: Entire. Texture, upper and lower surfaces: Smooth, glabrous. Color: When opening, upper and lower surfaces: Close to 66D. Fully opened, upper and lower surfaces: Close to 66D; towards the margin, close to 155D.

*Sepals, fertile flowers.*—Quantity/arrangement: Five in a single whorl. Length: About 0.5 mm. Width: About 1 mm. Shape: Broadly acute to deltoid. Apex: Acute. Base: Fused. Margin: Entire. Texture, upper and lower surfaces: Smooth, glabrous. Color, upper and lower surfaces: Close to 187C.

*Sepals, sterile flowers.*—Quantity/arrangement: Four in a single whorl. Length: About 3 cm. Width: About 3 cm. Shape: Broadly obovate. Apex: Obtuse to retuse. Base: Cuneate. Margin: Entire. Texture, upper and lower surfaces: Smooth, glabrous. Color: When opening and fully opened, upper surface: Close to 57C. When opening and fully opened, lower surface: Close to 66D.

*Peduncles, fertile and sterile flowers.*—Angle: Erect to about 20° from vertical. Strength: Strong. Length: About 5 cm. Diameter: About 3 mm. Texture: Smooth, glabrous. Color: Close to 187C.

*Pedicels, fertile flowers.*—Angle: About 20° to 30° from vertical. Strength: Strong. Length: About 4 mm. Diameter: About 2 mm. Texture: Smooth, glabrous. Color: Close to 187C.

*Pedicels, sterile flowers.*—Angle: About 30° from vertical. Strength: Strong. Length: About 3.5 cm. Diameter: About 2 mm. Texture: Smooth, glabrous. Color: Close to 187C.

*Reproductive organs, fertile flowers only.*—Stamens: Quantity per flower: About six. Anther length: About 0.5 mm. Anther shape: Oblong. Anther color: Close to 198C. Pollen amount: Moderate. Pollen color: Close to 198C. Pistils: Pistil quantity per flower: About two. Pistil length: About 1.5 mm. Stigma shape: Bi-parted.

Stigma color: Close to 66D. Style length: About 2 mm. Style color: Close to 66D.

*Seeds/fruits.*—Seed and fruit development have not been observed on plants of the new *Hydrangea.*

Disease/pest resistance: Plants of the new *Hydrangea* have not been observed to be resistant to pathogens and pests common to *Hydrangea.*

Temperature tolerance: Plants of the new *Hydrangea* have been shown to be tolerant to temperatures ranging from about −25° C. to about 38° C.

It is claimed:

1. A new and distinct *Hydrangea* plant named 'HorAbstra' as illustrated and described.

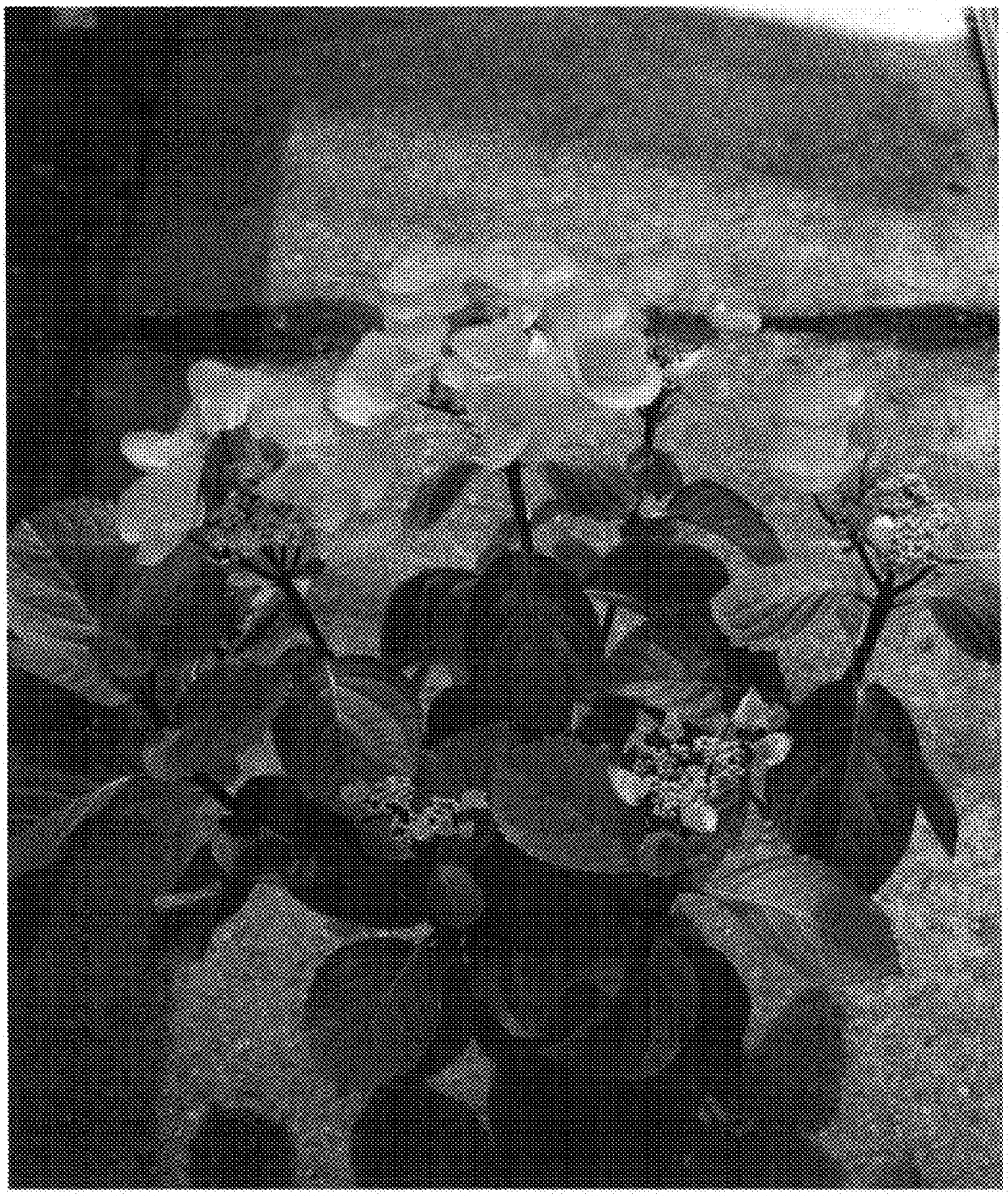

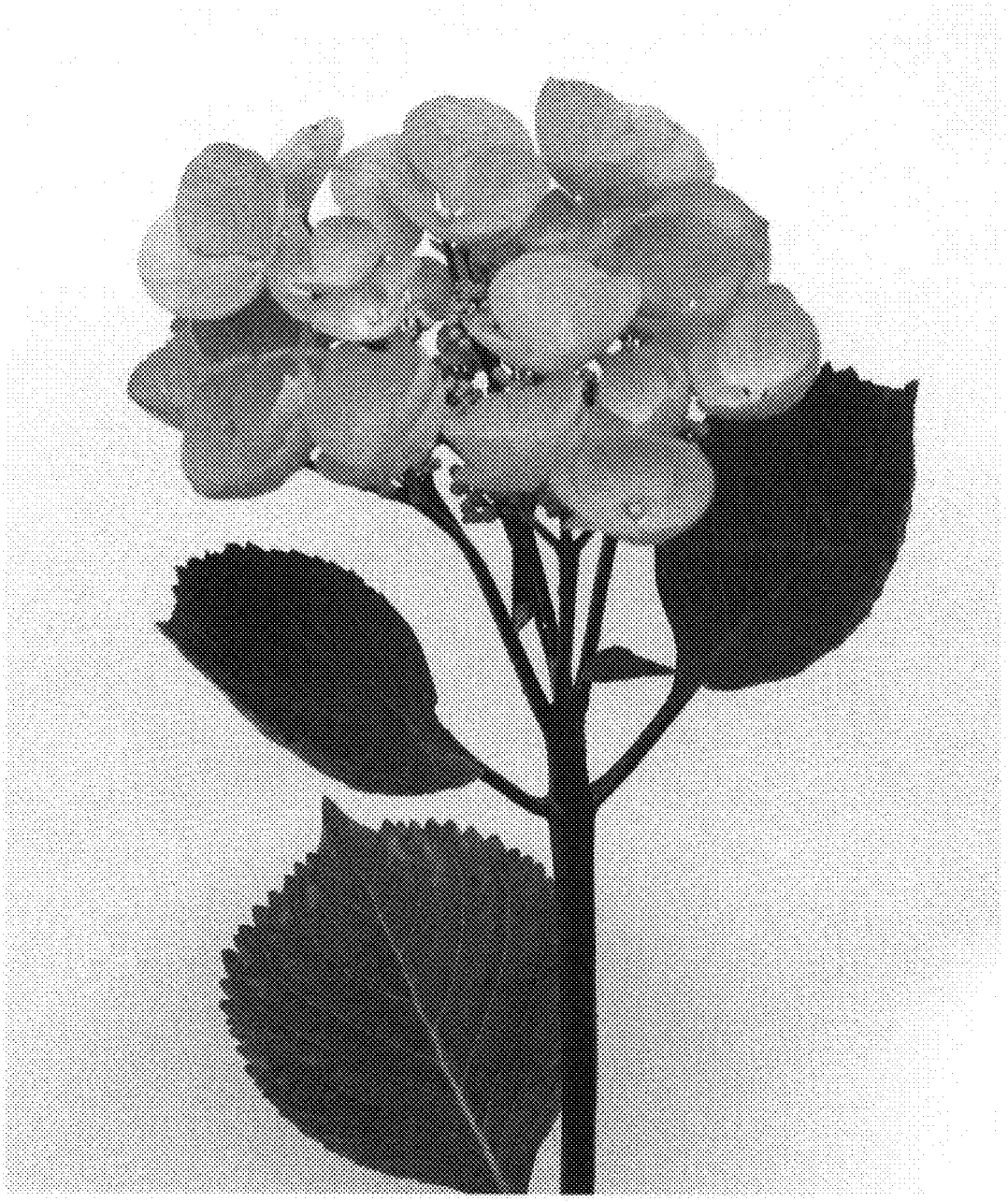

* * * * *